(12) United States Patent
Duchek et al.

(10) Patent No.: US 6,376,681 B1
(45) Date of Patent: Apr. 23, 2002

(54) SYNTHESIS OF COMPOUNDS USEFUL IN THE MANUFACTURE OF KETOROLAC

(75) Inventors: John R. Duchek, St. Louis; Henry J. Buehler, Affton, both of MI (US); Douglas C. Caskey, Stanley, NC (US)

(73) Assignee: Mallinckodt Inc., St. Louis, MO (US)

( * ) Notice: Subject to any disclaimer, the term of this patent is extended or adjusted under 35 U.S.C. 154(b) by 0 days.

(21) Appl. No.: 09/719,033

(22) PCT Filed: Jul. 8, 1999

(86) PCT No.: PCT/US99/15496

§ 371 Date: Dec. 6, 2000

§ 102(e) Date: Dec. 6, 2000

(87) PCT Pub. No.: WO00/02855

PCT Pub. Date: Jan. 20, 2000

Related U.S. Application Data

(60) Provisional application No. 60/092,408, filed on Jul. 10, 1998.

(51) Int. Cl.$^7$ .................. C07D 207/327; C07C 255/17; C07C 255/31
(52) U.S. Cl. .................. 548/561; 548/562; 558/432
(58) Field of Search .................. 548/561, 562; 558/432

(56) References Cited

U.S. PATENT DOCUMENTS 4,458,081 A * 7/1984 Joseph et al.
5,532,381 A * 7/1996 Yong et al.

FOREIGN PATENT DOCUMENTS

EP    0 000 649 A   *   2/1979
EP    0 486 807 A   *   5/1992

* cited by examiner

Primary Examiner—T. A. Solola
(74) Attorney, Agent, or Firm—Jeffrey S. Boone

(57) ABSTRACT

This invention relates to the drug, ketorolac and the synthesis of compounds useful in the manufacture of ketorolac. Ketorolac tromethamine is a pharmaceutical compound useful as an analgesic.

4 Claims, No Drawings

SYNTHESIS OF COMPOUNDS USEFUL IN THE MANUFACTURE OF KETOROLAC

This application is a 371 of PCT/US 99/15496 filed Jul. 8, 1999 which claims benefit of 60/092,408 filed Jul. 10, 1998.

BACKGROUND OF THE INVENTION

This invention relates to the drug, ketorolac and the synthesis of compounds useful in the manufacture of ketorolac. Ketorolac tromethamine is a pharmaceutical compound useful as an analgesic.

U.S. Pat. No. 4,087,539 and U.S. Pat. No. 4,089,969 (Muchowski; Syntex) teach the compound ketorolac and related compounds, and methods for their synthesis based on acetonedicarboxylate chemistry.

U.S. Pat. No. 4,140,698 (Van Horn; Syntex) teaches that 5-substituted-1,2-dihydro-3H-pyrrolo[1,2-a]pyrrole-1-carboxylic acids are prepared by hydrolysis from their corresponding nitriles. It teaches specifically the use of N-hydroxyethylpyrrole in a Mannich Reaction to synthesize a compound that can be useful in the synthesis of ketorolac.

U.S. Pat. No. 4,458,081 (Muchowski; Syntex) teaches that 5-substituted-1,2-dihydro-3H-pyrrolo[1,2-a]pyrrole-1-carboxylic acids are prepared by β-decarboxylation of the corresponding dialkly-1,1-dicarboxylates.

U.S. Pat. No. 5,082,951 (Muchowski; Syntex) teaches that 5-aroyl-2,3-dihydro-1H-pyrrolizine-1,1-dicarboxylates are prepared from 2-aroylpyrroles, and that hydrolysis and mono-decarboxylation of these compounds affords ketorolac and related compounds.

SUMMARY OF THE INVENTION

Briefly, the invention comprises several novel compounds useful in the synthesis of ketorolac, as well as methods of synthesizing ketorolac and its precursors.

DETAILED DESCRIPTION OF THE INVENTION

In this specification and claims, numerical values and ranges are not critical unless otherwise stated. that is, the numerical values and ranges may be read as if they were prefaced with the word "about" or "substantially".

A starting point in the synthesis of the compounds of interest is N-(2-bromoethyl) pyrrole ("BEP"). BEP is commercially available in at least small quantities. It can also be easily synthesized by the condensation of 2,5-dimethoxytetrahydrofuran ("2,5-DMT") and bromoethylamine hydrobromide ("BEA.HBr") as shown in reaction I.

(I)

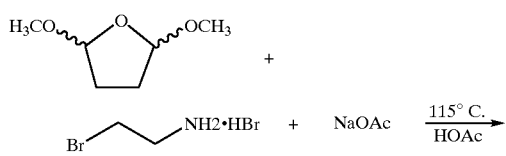

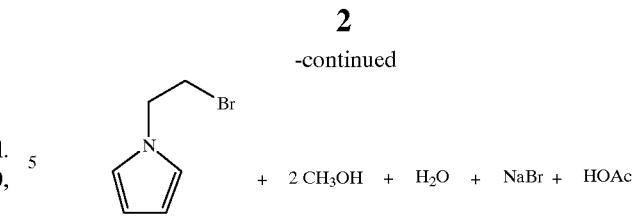

The novel compounds R 4-(N-pyrrolo)-2-cyanobutanoate ("R-PCB") can be produced by the alkylation of the R-cyanoacetate with BEP wherein R is an organic moiety that will not interfere with the subsequent reactions (the R moiety is ultimately removed in the production of ketorolac). Importantly, in this application the symbol "R" refers to an attached moiety and should not be interpreted as an indication of the stereochemistry of the molecule. Preferred R moieties include alkyl such as methyl, ethyl, propyl, iso propyl, and butyl, cyclo alkyl such as cyclohexyl, aromatic such as benzyl, and substituted analogs of the forgoing such as chloro or fluoro substituted. Preferred moieties are alkyl, with methyl and ethyl being more preferred and ethyl being most preferred. Thus, the most preferred species is ethyl 4-N-pyrrolo-2-cyanobutanoate ("EPCB"). This alkylation reaction preferably takes place in the presence of sodium ethoxide in ethanol at 85° C., as shown in reaction II (The sodium ethoxide is a strong base, used to deprotonate the ethyl-cyanoacetate. The resulting carbanion is alkylated by the BEP.)

(II)

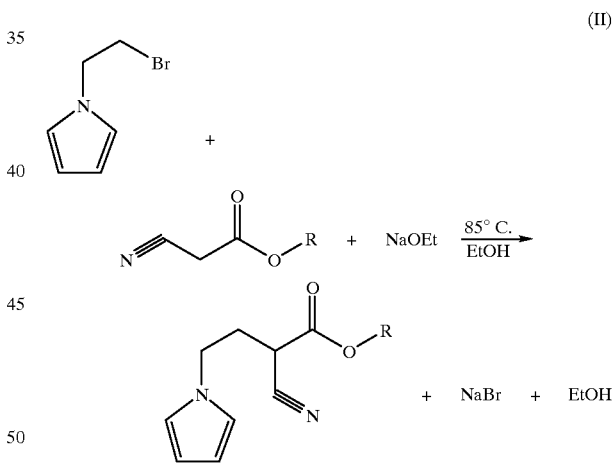

The resulting R-PCB (preferably EPCB) is a novel compound that is useful in the synthesis of ketorolac.

R-PCB (EPCB) can be used in a novel synthetic method where it is reacted in a modified Friedel-Crafts acylation with benzoyl chloride, as shown in reaction III, to produce the novel compounds R 4-N-(2'-benzoyl)pyrrolo-2-cyanobutanoate ("R-BPCB"), wherein R has the meaning given above. Thus, the preferred species is ethyl 4-N-(2'-benzoyl) pyrrolo-2-cyanobutanoate ("EBPCB").

(III)

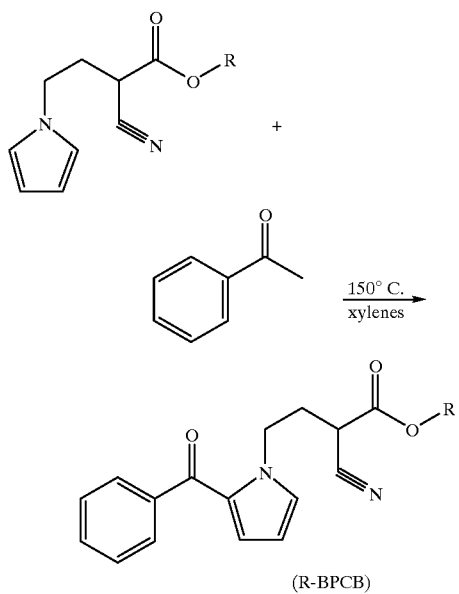

(R-BPCB)

In reaction III, it is important that no catalyst be used. While the use of a catalyst is typically standard in an ordinary Friedel-Crafts reaction, in the case of this reaction, the use of a catalyst will cause undesired side reactions (production of polymeric material and unwanted isomers). Mixing and heating the reaction mixture to boiling is also important to help expel HCl byproduct which would act as an undesired catalyst. The temperature is desirably 120 to 180° C., preferably 140 to 160° C., more preferably 145 to 155° C., and ideally 150 to 155° C. It has been found that xylenes are an exemplary reaction medium. Xylenes will normally undergo Friedel-Crafts reaction, but in the modified Friedel-Crafts reaction conditions of this invention, the xylenes do not react.

R-BPCB (EBPCB) is useful in a novel reaction in which it is cyclized as shown in reaction IV:

(IV)

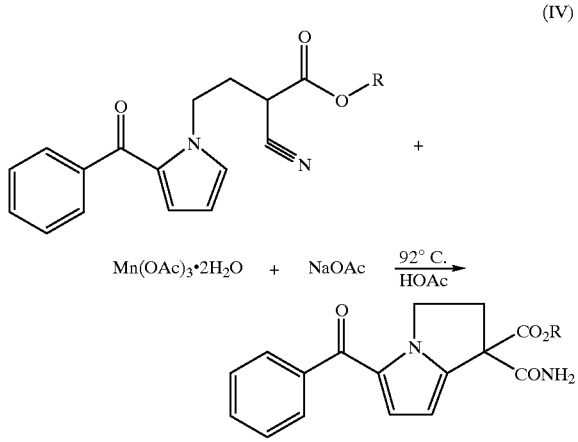

In reaction IV, R-BPCB (EBPCB) is reacted with a compound of high oxidative potential that is capable of promoting a single electron transfer. By "high oxidative potential" is meant 1.54 electron volts or greater. Suitable such compounds of high oxidative potential capable of single electron transfer include $Ce^{3+}$, $Mn^{3+}$ compounds. An exemplary compound is $(CH_3C(O)O)_3Mn.2H_2O$. Suitable solvents include EtOH, MeOH & HOAc, with acetic acid being preferred. Similar reactions (see Artis et al., Chem Rev. 1996, 96, p. 352–353) teach the use of temperatures of 20 to 80° C., but it has been discovered that novel reaction IV is desirably run at temperatures above 80° C., preferably 85 to 118° C., more preferably 90 to 100° C., and most preferably 92 to 95° C.

After cyclization of the R-BPCP, the resulting product ethyl-5-Benzoyl-1,2-dihydro-3H-pyrrolo [1,2a] pyrrole-1-carboxamide, 1-carboxylate (structure given below) is easily subjected to hydrolysis with a strong base such as sodium hydroxide, as shown in reaction V-a to yield the novel compound 5a sodium 5-benzoyl- 1,2-dihydro-3H-pyrrolo[1,2-a]pyrrole-1-carboxamide-1-carboxylate.

(V-a)

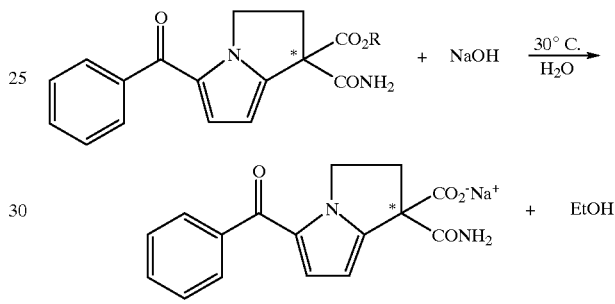

5-a is easily decarboxylated with a strong acid such as hydrochloric acid, as shown in reaction V-b, to yield the novel compound 5-benzoyl-1,2-dihydro-3H-pyrrolo-[1,2-a] pyrrole-1-carboxamide ("ketorolac carboxamide").

(V-b)

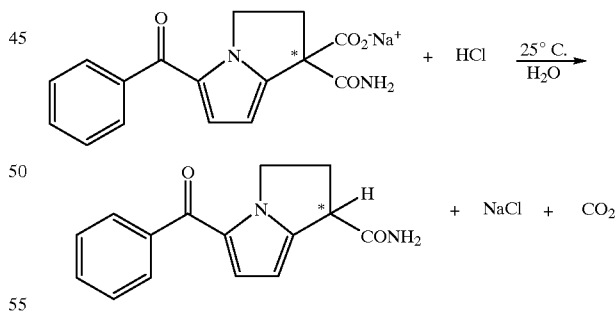

The "ketorolac carboxamide" is in turn easily hydrolyzed by anyone skilled in the art by reacting with first a strong base such as sodium hydroxide and then a strong acid such as hydrochloric acid to convert to the acid, as shown in reaction V-c, to yield 5-benzoyl-1,2-dihydro-3H-pyrrolo-[1,2-a]pyrrole-1-carboxylic acid (ketorolac free acid). Ketorolac free acid can be formulated directly or can be converted to the tromethamine salt by reaction with tromethamine $(H_2NC(CH_2OH)_3)$ according to known processes.

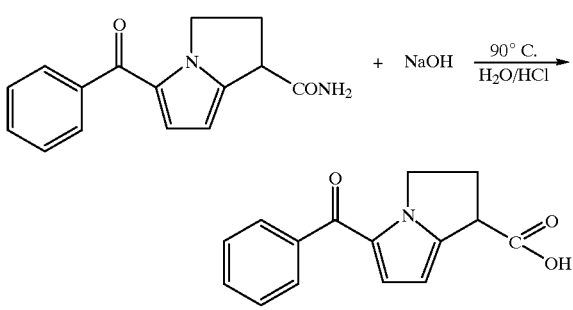

In order that those skilled in the art may understand our invention, the following examples are given by way of illustrations and not by way of limitation.

EXAMPLE 1

Step 1. Condensation of 2,5-Dimethoxytetrahydrofuran and 2-Bromoethylamine Hydrobromide (Not an Example of the Invention)

A well $N_2$-purged 2-liter reactor equipped with overheads configured for total reflux is charged with 67.3 g of sodium acetate (anhydrous) and 1166 g of glacial acetic acid. The agitated solution is heated to 115–117° C. at which time the 92.6 g BEA.HBr is added. Next, 61.7 g of 2,5-DMT is added.

The reaction is essentially instantaneous. Once the reaction is complete the crude product is isolated by removing the majority of the acetic acid by either neutralization or distillation.

190 g of toluene is added to the reduced mass and the mass is cooled to as low a temperature as possible. 258 g of ice and 425 g of DI water is added to drop the temperature of the solution down to −15° C.

To the cooled solution 0.22 L of 50% NaOH was slowly added at such a rate as to maintain the solution temperature below 30° C. The actual amount of NaOH required for neutrality will be based on the extent (if any) of the acetic acid removed by distillation.

The resultant phases are allowed to settle for 30–60 minutes. The bottom aqueous phase may require one or two 0.13 L back washes of toluene to remove any solubilized product. The organic layers are combined for a total volume of ~0.49 L.

The organic phase is placed in a 0.5 L distillation vessel equipped with 1–2 theoretical plates and vacuum capabilities down to 5 mm Hg (66 Pa). A forecut of toluene is collected and heartcut collected at a pot temperature of 63° C. and an overhead temperature of 62° C. with a 1 to 1 reflux ratio under 5 mm Hg pressure. The distillation is complete after pot and overheads temperatures of 96 and 64.5° C. respectively, have been obtained. (Note: care should be taken to prevent thermal decomposition of the product during distillation).

The distillation produces 53 g of pure N-2-bromoethylpyrole.

Step 2. Alkylation of Ethyl Cyanoacetate with N-2-Bromoethylpyrrole (Example of the Invention)

A dry 2-L flask equipped with a condenser is charged with 180 g of BEP and 936 g of ethyl cyanoacetate (ECA). The solution is agitated and heated to 81–85° C. The 351 g sodium ethoxide (21% (weight) solution in ethanol) is added over a period of 40 minutes when the temperature reaches 40° C.

The reaction is complete generally in 1–2 hours when good quality NaOEt is used.

Once the reaction is determined to be complete, the solution is cooled down to 20–25° C. and washed with 1×0.5 L of water and 1×0.5 L saturated NaCl. The 1 L (1012 g) of organic phase is placed in a distillation vessel capable of reflux and operating conditions of 200° C. and 4.5 mm Hg pressure. The distillation of the crude product will need to done using a distillation apparatus with 2–3 theoretical plates and distillation temperature and pressure capabilities of 200° C. and 4.5 mm Hg, respectively. Approximately 172 g (0.16 L) of high purity product will be collected.

Note 1: This compound has been shown to be prone to thermal degradation at temperatures above 200° C.

Step 3. Friedel-Crafts Acylation of Ethyl 4-N-pyrrolo-2-cyanobutanoate With Benzoyl Chloride (Example of the Invention)

A dry 2-L well baffled and mixed flask equipped with reflux capabilities is charged with 170 g of EPCB, 250 g of benzoyl chloride and 493 g of xylenes. The solution is well mixed and heated to reflux temperature of 150–155° C. for 13–16 hours. The rate of this reaction and its impurity profile is extremely sensitive to the expulsion rate of the by-product HCl. To that end it is imperative that significant boil up rate and the best mixing possible is -maintained to aid in the expulsion of HCl.

Once the reaction has been determined to be complete, as a result of the disappearance of starting material, the product needs to be isolated from the excess benzoyl chloride and xylenes solvent.

The isolation is achieved by quenching the reaction with 200–300 g of anhydrous ethanol (100% or denatured without methanol) at 80° C. for 1 hour. When the quench is complete the excess ethanol, xylenes and ethyl benzoate (the product of the quench of benzoyl chloride and ethanol) are distilled off under reduced pressures.

The low boiling ethanol and xylenes are readily distilled off. The final pot conditions required to remove the relatively high boiling ethyl benzoate are 115° C. and 7 mm Hg. The distillation residuals (as a thick oil) are assayed for weight percent composition and ready for use in the ring closure step.

(Note: An alternative isolation procedure is to remove the excess benzoyl chloride by reacting it with sodium glycinate, and then crystallizing the EBPCB.)

Step 4. $Mn^{3+}$ Promoted Oxidative Free Radical Cyclization of Ethyl 4-(N-(2'-benzoylpyrrolo)-2-cyanobutanoate (Example of the Invention)

A dry 2-L well baffled and mixed flask equipped with reflux capabilities is charged with 147.3 g of $Mn(OAc)_3 2H_2O$, 30.6 g of sodium acetate anhydrous, 56.7 g of EBPCB and 1377 g (0.344 gal.) of glacial acetic acid. The reaction mix is heated to 92° C. with good mixing.

The reaction is sampled over the course of 30–48 hours to monitor the rate of the reaction. Once the reaction is considered complete, greater than 95%, the solution is cooled down to 15° C. and the spent solids are readily filtered through a 30 μ filter pad. The solids ($Mn(OAc)_2 4H_2O$) are washed with cold glacial acetic acid and the filtrates are combined.

The 1.5 L of combined acetic acid solutions are placed in a clean distillation vessel equipped with a condenser. The mass is reduced ~70–90% (preferably by about 85%) to a volume of 0.15–0.45 L. The final distillation conditions are a pot and overhead temperature of 57° C. and 46° C. respectively, at 30 mm Hg pressure.

The still bottoms from the strip is the feed for the next step, the ester hydrolysis, decarboxylation and amide hydrolysis to create the crude ketorolac acid.

Step 5. Isolation of Crude Ketorolac Free Acid

Step 5(a) Hydrolysis (Example of the Invention)

The still bottoms generated from Step 4 are diluted with 250 g of ethanol or methanol when the temperature of the still bottoms dropped below 60–70° C. The hot solution is transferred to a clean 2-L flask for hydrolysis.

The ethanolic solution is diluted with 1047 g of deionized water. The pH of the solution is adjusted to 12 with the addition of 120–125 g of 50% NaOH. The heat of neutralization raised the solution temperature to 30° C. External heating was applied to maintain the temperature at 30° C. for 1 hour to ensure complete hydrolysis.

Step 5(b). Decarboxylation (Example of the Invention)

Decarboxylation is accomplished by adjusting the pH of the solution down to a pH of 2 by adding of 150 g of concentrated HCl. The decarboxylation is rapid and complete as evident by the fact that all the $CO_2$ off gassing is complete within 5 minutes.

Step 5(c). Hydrolysis

The hydrolysis of the amide is achieved by adjusting the solution from a pH of 2 to an approximate pH of 13.25 by the addition. of 255 g of 50% NaOH. The solution is heated to a temperature of 90–95° C. for 30 minutes to drive the amide hydrolysis to completion. The reactor's overheads are configured to collect ~300–500 g of ethanol/water/ammonia distillate over the 30 minute digest period. Vacuum is applied to assist this strip.

The isolation of the crude ketorolac acid is carried out by adjusting the pH of the solution down to pH of 4 by the addition of 216 g of concentrated HCl. When the pH of the solution is near neutrality (pH 7–8) the HCl addition is stopped and 3.95 kg of Darco G60 activated carbon is added. Approximately an equal weight of diatomaceous-earth type filter-aid is added to facilitate the filtration. The solution is stirred at the neutralization temperature (25–30° C.) for 30–60 minutes and the carbon is removed. The pH of the filtrate is lowered to pH of 4 by the addition of glacial acetic acid.

The solution is cooled down and stirred for 30 minutes at 5° C. The solids are collected on a 35 μm pad and dried for 8–16 hours at 65° C. under 100 mm Hg pressure. The dried crude ketorolac acid is recovered for further processing.

What is claimed is:

1. A compound of the formula:

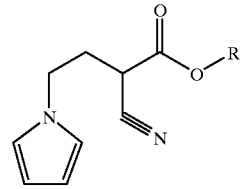

(C-II)

wherein R is an alkyl, cycloalkyl, or aromatic moiety, or a substituted alkyl, cyclo alky, or aromatic moiety.

2. The compound of claim 1 wherein R is an alkyl moiety.
3. The compound of claim 2 wherein R is methyl or ethyl.
4. The compound of claim 3 wherein R is ethyl.

* * * * *

UNITED STATES PATENT AND TRADEMARK OFFICE
CERTIFICATE OF CORRECTION

PATENT NO.    : 6,376,681 B1
DATED         : April 23, 2002
INVENTOR(S)   : John Duchek and Henry Buehler It is certified that error appears in the above-identified patent and that said Letters Patent is hereby corrected as shown below:

Column 13,
Lines 10-15, the structure

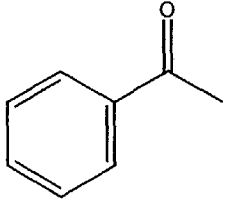

should be replaced with the structure

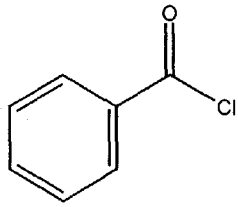

Signed and Sealed this

Fifth Day of August, 2003

JAMES E. ROGAN
*Director of the United States Patent and Trademark Office*